(12) United States Patent
Hasselberg

(10) Patent No.: US 7,596,252 B2
(45) Date of Patent: Sep. 29, 2009

(54) METHOD FOR POST-EDITING A MEDICAL IMAGE DATA SET

(75) Inventor: Birgit Hasselberg, Neunkirchen A. Brand (DE)

(73) Assignee: Siemens Aktiengesellschaft, Munich (DE)

( * ) Notice: Subject to any disclaimer, the term of this patent is extended or adjusted under 35 U.S.C. 154(b) by 781 days.

(21) Appl. No.: 10/937,262

(22) Filed: Sep. 10, 2004

(65) Prior Publication Data

US 2005/0058329 A1    Mar. 17, 2005

(30) Foreign Application Priority Data

Sep. 11, 2003    (DE) .............................. 103 42 015

(51) Int. Cl.
    *G06K 9/00* (2006.01)
(52) U.S. Cl. ..................... 382/128; 128/922; 378/4
(58) Field of Classification Search ............... 382/100, 382/128–133, 162–167, 232, 243, 244, 254–308; 715/500, 517–530, 724; 128/922; 378/4–27
See application file for complete search history.

(56) References Cited

U.S. PATENT DOCUMENTS

| 5,150,427 A * | 9/1992 | Frazee et al. ................ 382/131 |
| 7,020,868 B2 * | 3/2006 | Debbins et al. ............. 717/108 |
| 7,269,303 B2 * | 9/2007 | Miller et al. ................ 382/305 |
| 2001/0051881 A1 * | 12/2001 | Filler ............................ 705/3 |
| 2003/0142859 A1 * | 7/2003 | Okuzawa .................... 382/132 |

FOREIGN PATENT DOCUMENTS

GB    2 382 509 A    5/2003

OTHER PUBLICATIONS

German office action filed on Nov. 21, 2006 by applicant.*
Ann Redelfs, "SDSC Releases Version 3.0 of the Portable SDSC Image Tools", Oct. 11, 1995, Site 1. vol. 2 and San Diego Supercomputer Center Image Tools Release Notes 3.0, Aug. 1995, pp. 1-7.
National Electrical Manufacturers Association, "Digital Imaging and communications in Medicine (DICOM)" Part 1: Introduction and Overview, PS 3.1-2000, pp. 1-13.
"Scalable Visualization Toolkits for Bays to Brains", The Scripps Research Institute, National Partnership for Advanced computation Infrastructure (NPACI), 2000-2003.

* cited by examiner

*Primary Examiner*—Anand Bhatnagar
(74) *Attorney, Agent, or Firm*—Harness, Dickey & Pierce, PLC

(57) ABSTRACT

A method is for post-editing a first image data set using a post-editing software program, the image having initially been obtained using an image producing medical examination device, and a second post-edited image data set including an image attribute, which characterizes the post-editing of the second image data set. The second image data set is loaded into the post-editing software, whereby there the image attribute is extracted from the second image data set and buffered. The first image data set is then post-edited by transferring the buffered image attribute onto it. An advantage of the method lies in the fact that the post-editing and display of the first image data set occur in a quick and simple manner.

23 Claims, 2 Drawing Sheets

METHOD FOR POST-EDITING A MEDICAL IMAGE DATA SET

The present application hereby claims priority under 35 U.S.C. §119 on German patent application number DE 103 42 015.0 filed Sep. 11, 2003, the entire contents of which are hereby incorporated herein by reference.

FIELD OF THE INVENTION

The invention generally relates to a method for post-editing a first image data set using a post-editing software program. Preferably, the image has initially been obtained using an image producing medical examination device.

BACKGROUND OF THE INVENTION

The use of image producing medical examination devices enables the production of high-resolution images of an examination object, mostly within areas of a human body. For example, it is possible to carry out anatomical, morphological or functional recordings. These can represent the area recorded in two or three-dimensional images. Furthermore, the use of the so-called functional image production facilitates the portrayal of a process changing with time, such as a physiological function or a pathological process. In this way, the structure of organs and tissues is repeatedly scanned in order to carry out, for example, a dynamic examination of the movement of the heart, joints or the fluid in the brain.

Image data sets of this type can essentially be obtained using different image producing techniques available in medicine, such as sonography, computer tomography, angiography or magnetic resonance tomography.

When an image data set obtained from an image producing medical examination device is post-edited, the image data set to be post-edited is usually loaded into a post-editing software program. This software uses a number of image attributes that have to be set (parameters), in order to determine the way it is to be presented. The parameters are usually set manually using the view resulting from the image data set loaded. Post-editing software of this type may also offer standard parameter settings, which serve as a starting point for the manual view and which are permanently stored in the software. In most cases a user of the post-editing software is also able to store his/her own presettings in the post-editing software.

An example for this type of software are the VisTools, such as are outlined, for example, in the paper "Scalable Visualization Toolkits for Bays to Brains", NPACI, Alpha Project Review Meeting, Jan. 2001, and which are a successor of the "San Diego Image Tools", Version 3.0, 11th Oct. 1995. Here, for example, the parameters in the image view are set using the 'imadjust function' (image adjust).

Now standards have been developed for the patient information system for medical devices, the standards allowing data to be transmitted and saved in a heterogeneous infrastructure as is found in a clinic, a medical practice or in a medical laboratory, involving no loss of information, even if the intercommunicating appliances cannot, in part, understand the information transmitted. The availability of certain information in a standardized format for transmitting and storing is sufficient, e.g. address information, information on the data type etc.

An example of this kind of standard is the DICOM-Standard (DICOM=Digital Imaging and Communication in medicine, see, for example, "Part 1: Introduction and Overview", PS 3.1-2000, National Electrical Manufacturers Association, 2000). The DICOM-Standard standardizes the structure of the formats and descriptive parameters for radiological images and commands for exchanging these images, and also the description of other data objects, such as image sequences, examination series and findings. The description of different methods of data compressions is also defined in the DICOM-Standard.

Roughly speaking, it differentiates between three different areas or blocks. An initial general block with a fixed definition, which is obligatory for all producers and modalities, includes instructions as to the ordering and distribution of data. Furthermore, a modality specific block is defined which is obligatory for all producers. In the case of magnetic resonance image production, for example, the parameters used for this can be found in this block (echo time, repetition time etc.). Finally there is a proprietary block that each producer can complete for his/her own purposes.

SUMMARY OF THE INVENTION

An object of an embodiment of the invention is to simplify and in particular to speed up the post-editing of images taken with image producing medical devices.

An object may be achieved in accordance with an embodiment of the invention by a method for post-editing a first image data set attained from an image producing medical device, using a post-editing software and a second post-edited image data set having an image attribute that characterizes the post-editing of the second image data set. The second image data set is loaded into the post-editing software, whereby, there the image attribute is extracted from the second image data set and buffered. Finally, the first image data set is post-edited by transferring the buffered image attribute into it.

One of the image data sets can, for example, be generated for image production using the method mentioned specified at the start, for example using magnetic resonance or computer tomography devices. One of the image data sets can, for example, be a 3D image data set, a dynamic, an anatomical, a morphological or a functional image data set. The post-editing software can either be integrated into the examination device, or it can be installed as a stand-alone, for example, on a dedicated post-editing unit.

An image data set is displayed by setting image attributes with the aid of the post-editing software. These image attributes are parameters which characterize special characteristics of the manner in which it is presented, i.e. of the post-editing. For example, an image attribute can be a descriptive parameter for a filter value or a contrast, color or 3D effects, e.g. a corresponding ramp setting. Furthermore, a section which is to be post-edited and displayed can, to a certain extent, be defined as an image attribute. Correspondingly, a viewing direction on a 3D display can also be stored as an image attribute in the image data set.

An advantage of the method lies in the fact that the post-editing and display of the first image data set can be carried out in a simple and rapid manner, i.e. without being time-consuming for the user. This is based on the fact that already existing data sets and evaluation processes are used, in particular with 3D displays. The automatic inheritance of one or a plurality of image attributes renders the laborious clicking and setting of the different parameters superfluous. This results in high workflow efficiency. The method also allows an additional saving of time, when it is adopted as a partial aspect in an automated sequence chain in the operation of an image producing examination device, thus leading to workflow automation.

A further advantage of an embodiment of the method lies in the fact that it enables an identical image impression to be transferred consistently from one data set to another.

A further advantage of an embodiment of the method lies in the fact that it allows a simple exchange of knowledge by way of post-editing image data sets. For example, a special type of image post-editing, which was, for example, created by a developer of the post-editing software and which facilitates diagnosis by setting special viewing focuses, can be made available to an external user. This harbors the possibility of exchanging experiences in post-editing worldwide.

A further advantage of an embodiment of the method lies in the fact that it supports standardization of displays of examinations using image producing examination devices. For example, this simplifies the work of several operators at one examination device, the exchange of information between universities or the operation of different examination devices at different locations by one and the same operator.

Furthermore an embodiment of the method is advantageous in improving the repeatability of studies or post examinations. It enables and simplifies the quality control of image producing examinations, as an identical display of the respective examination is generated in each case. This means that errors, for example, in the examination device or in the post-editing unit are detected more quickly.

In one particular embodiment of the method, one or a plurality of buffered image attributes are stored as a post-editing template in the post-editing software. This has the advantage that after the second image data set has been loaded, the information (image attributes) can be stored locally by the post-editing software, so that it can be repeatedly retrieved, can be quickly accessed and is easily transferred.

In a particularly advantageous embodiment of the method, one of the image data sets and one or a plurality of the buffered image attributes are stored in a file in the DICOM medical communication standard. This has the advantage that all the information in the file is merged together according to the DICOM standard, i.e. all parameters relating to the display and the image information (e.g. on a pixel basis) are stored together. These parameters, for example, the special filter and ramp settings, are preferably stored in the proprietary block of the DICOM standard, the block being used by each manufacturer for his/her own purposes. A further advantage to merging the information together in one file lies in the facilitated data transfer of the required information and the simple exchange of image attributes.

In an advantageous embodiment of the method, the second image data set is downloaded from an external image gallery, in particular via an Internet link. This has the advantage that the knowledge of special post-editing and display types can be transferred rapidly from external image galleries to the user's own image data sets.

In a particularly advantageous development of an embodiment of the method, one or a plurality of buffered image attributes is allocated to a protocol for image recording using the image producing medical examination device and a data set obtained using the protocol is displayed using the allocated image attribute(s). The advantage of this is the high workflow automation of an examination, the protocol or which being supplemented in this way.

BRIEF DESCRIPTION OF THE DRAWINGS

Further advantages, features and details of the invention will become evident from the description of illustrated exemplary embodiments given hereinbelow and the accompanying drawings, which are given by way of illustration only and thus are not limitative of the present invention, wherein.

DETAILED DESCRIPTION OF THE PREFERRED EMBODIMENTS OF THE INVENTION

Figure 1:
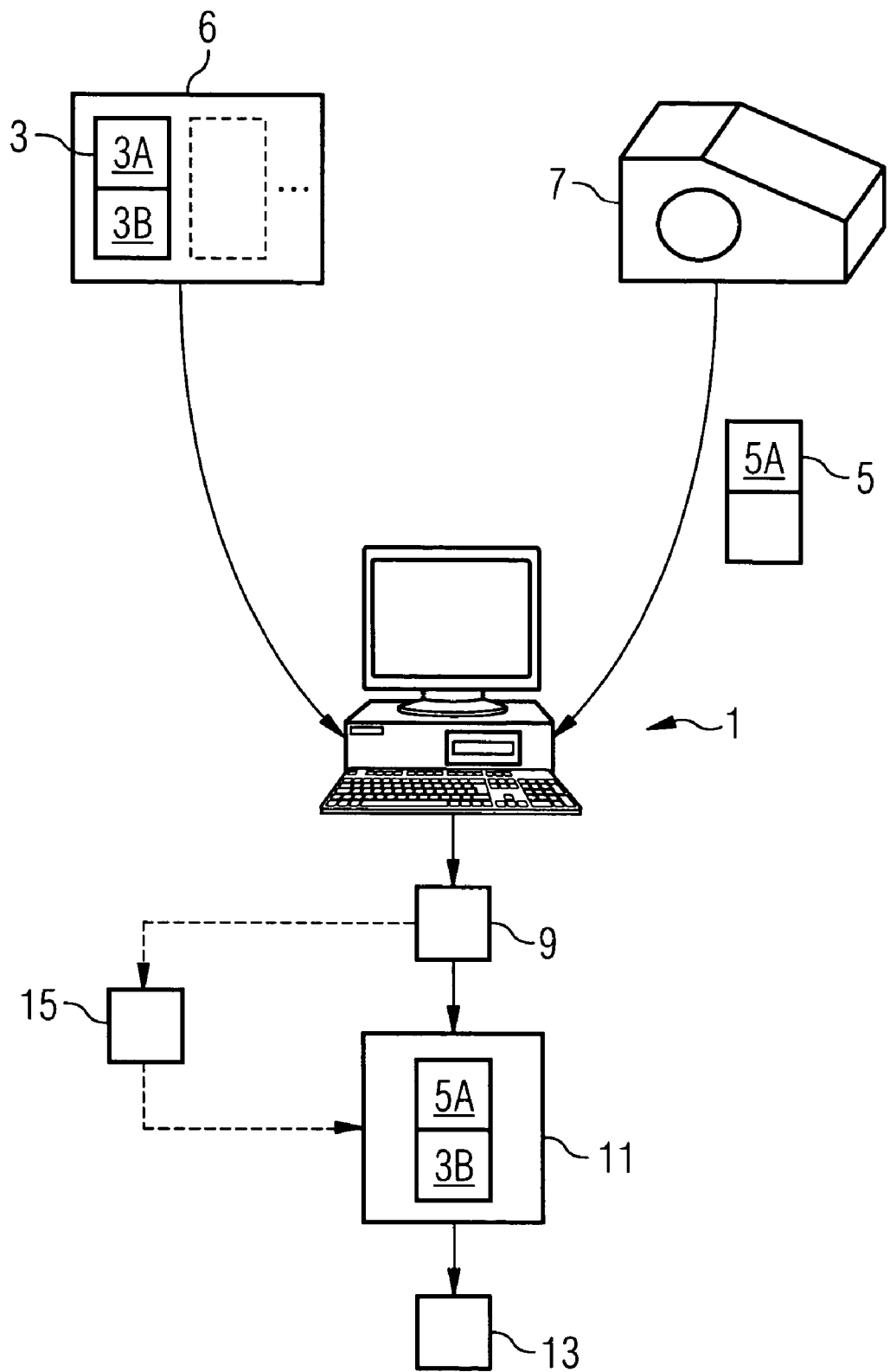
FIG. 1 shows a flow chart to clarify the process sequence.

FIG. 1 shows a flow chart to clarify the method according to an embodiment of the invention. A post-editing software program for post-editing and displaying image data sets taken using image producing examination devices is installed on a computer. The method according to an embodiment of the invention enables the transmission of a display manner from a model data set 3 to another data set 5. In this way, any display of any arbitrary data set can be used as a model. The special display manner is, for example, a three dimensional view of a vascular examination or a coloscopy examination.

The user of the post-editing software obtains the model data set 3, for example, by downloading from the Internet or the local network, by e-mail or as a copy on a data carrier. In FIG. 1 the user of the post-editing software downloads the model data set 3, for example, from a database 6 of a university, a colleague or from a manufacturer of an examination device. The model data set 3 comprises a first area, which contains, for example, pixel based image information 3A, and a second area comprising image attributes 3B of the image data set, the attributes determining the way in which the image information is displayed when the post-editing software is used. The image attributes 3B define, for example, what is referred to as a wetlook display of a 3D data set or they define parameters of the windows or ramp progressions. The model data set 3 is preferably stored in a standardized format, for example, in the DICOM format.

The user of the post-editing software would now like to display an image data set 5 in exactly the same way, which he/she has recorded, for example, with a computer tomography device, magnetic resonance device or ultrasound device 7.

If the image data set 5 which is to be post-edited and displayed is available on the computer 1, extraction 9 of the image attributes 3B can be initiated by moving the image data set 5 onto the model data set 3, acting as a model, by way of Drag & Drop for example. The image attributes 3B are buffered in computer 1 and are subsequently transferred to the image data set 5 which is to be post-edited (Step 11). Finally a display 13 of the image data set 5 is effected in accordance with the image attributes 3B.

Furthermore, the parameters or the model data set 3 can be inherited into a local database 15 to make them accessible more rapidly and in larger quantities for post-editing further data sets.

In an alternative procedure of the method according to an embodiment of the invention, it is possible to use Drag & Drop to load an image of an earlier examination from the Explorer directly into the post-editing software. This software extracts the image attributes, buffers them and transfers them onto the image data set 6. In this way, the method simplifies the display and post-editing and increases the diagnostical safety e.g. in follow-up checks or pre- and postoperative questions.

The functionality of an embodiment of the method preferably uses image data sets that were examined using the same examination device and post-edited with the same software.

Standardizations or conversion routines also enable the method to be extended to include different types of examination devices.

With the integration of a method into an automated sequence chain during the operation of an image producing examination device, this can result in an advantageous, time saving workflow automation, combining a measurement report with a targeted display.

Figure 2:
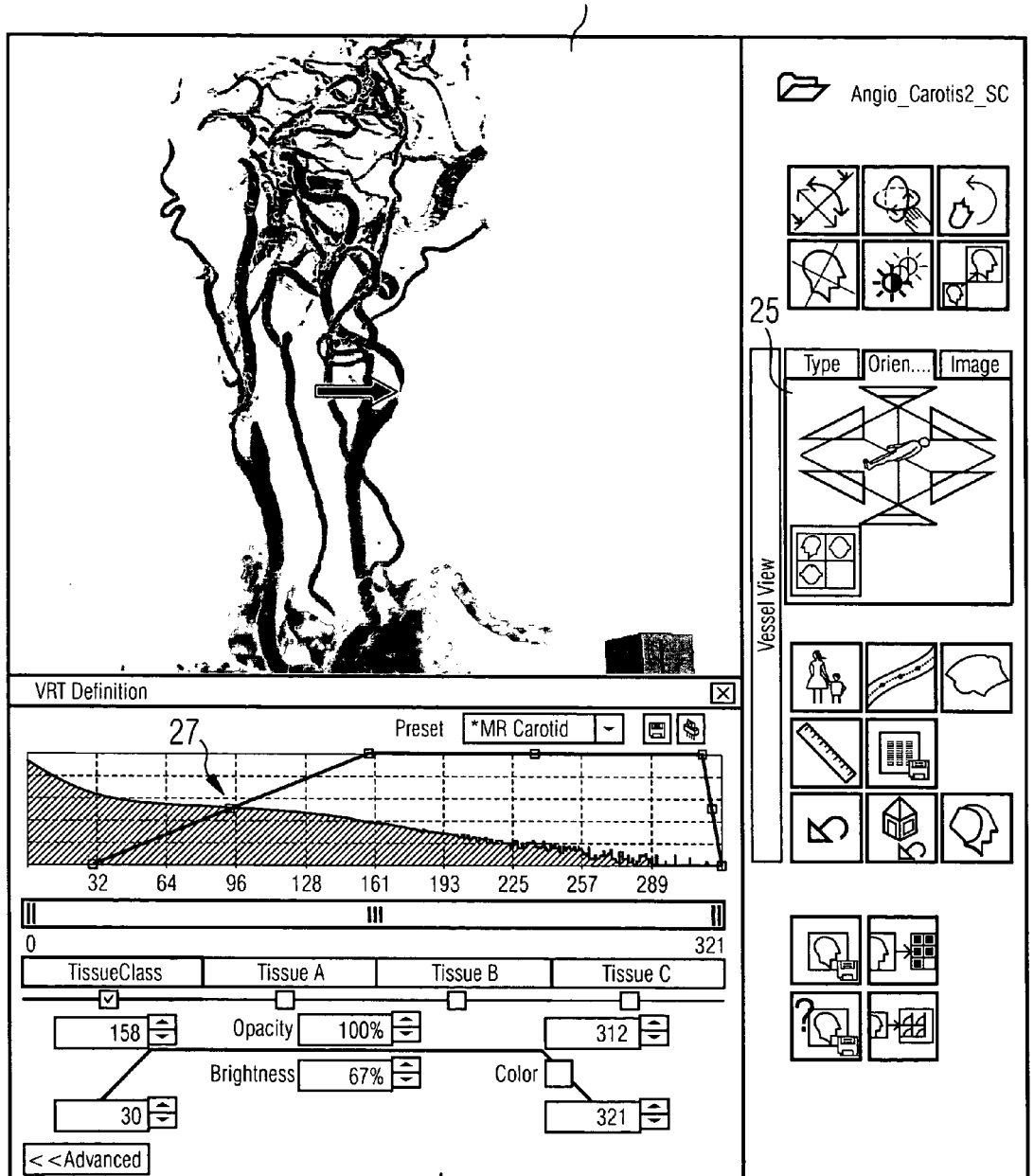
FIG. 2 shows an exemplary user interface of a post-editing software program.

FIG. 2 shows a user interface of a post-editing software program according to the invention. The user interface displays several windows, for example, a window 21 with a vessel display, a window 23, which is used for inputting image attributes, and including a window 25 for adjusting an angle of view on the 3D data set presented. For example, a ramp with starting value "30" and end value "158" in the grey gradation of the basic data set is displayed in window 23. In addition to the exemplary pixel based image data, the ramp setting 27 is stored in an image data set, preferably in a DICOM standard. When the attributes of the model data set are loaded, all the attributes that describe the post-editing, are automatically transferred by the post-editing software to the new image data set that is to be displayed. The image attributes include, for example, the respective section of the image data displayed the viewing direction, filter values, ramp settings of contrast, color and 3D effects.

Any of the aforementioned methods may be embodied in the form of a program. The program may be stored on a computer readable media and is adapted to perform any one of the aforementioned methods when run on a computer. Thus, the storage medium or computer readable medium, is adapted to store information and is adapted to interact with a data processing facility or computer to perform the method of any of the above mentioned embodiments.

The storage medium may be a built-in medium installed inside a computer main body or removable medium arranged so that it can be separated from the computer main body. Examples of the built-in medium include, but are not limited to, rewriteable involatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Method for post-editing of a first image data set, obtained using an image producing medical device with the aid of a post-editing software program, and a second post-edited Image data set including an image attribute which characterizes the post-editing of the second image data set, the method comprising:
    loading the second image data set so that the post-editing software program can extract the image attribute from the second image data set;
    buffering the image attribute; and
    loading, post-editing and displaying the first image data set by transferring the buffered image attribute to the first image data set.

2. Method according to claim 1, wherein at least one of a plurality of image attributes are buffered and stored as post-editing templates in the post-editing software.

3. Method according to claim 1, wherein one of the image data sets and the buffered image attribute are stored in a file in the medical communication standard DICOM.

4. Method according to claim 1, wherein the second image data set is downloaded from an external image gallery.

5. Method according to claim 1, wherein the second image data set is downloaded via a data link from a remote storage medium.

6. Method according to claim 1, wherein the buffered image attribute is allocated to a protocol for image recording using the image producing medical device and wherein a data set obtained with the protocol is displayed using the allocated image attribute.

7. Method according to claim 1, wherein at least one of at least one filter value and at least one ramp setting of at least one of contrast, color and 3D effect is defined as an image attribute.

8. Method according to claim 1, wherein a detail is defined as image attribute, which section is post-edited.

9. Method according to claim 1, wherein a viewing direction is defined as an image attribute.

10. Method according to claim 1, wherein one of the image data sets is a 3D image data set.

11. Method according to claim 1, wherein one of the image data sets is at least one of an anatomical, a morphological and a functional image data set.

12. Method according to claim 1, wherein one of the image data sets is generated using at least one of a magnetic resonance and computer tomography device.

13. Method according to claim 1, wherein at least one of a plurality of image attributes are buffered.

14. Method according to claim 13, wherein one of the image data sets and at least one of the buffered image attributes are stored in a file in the medical communication standard DICOM.

15. Method according to claim 13, wherein at least one of the buffered image attributes is allocated to a protocol for image recording using the image producing medical device and wherein a data set obtained with the protocol is displayed using the allocated at least one image attribute.

16. Method according to claim 1, wherein the second image data set is downloaded from an external image gallery by way of an Internet connection.

17. Method according to claim 1, wherein one of the image data sets is a dynamic image data set.

18. A program recorded on a computer-readable medium, adapted to perform the method of claim 1, when executed on a computer.

19. An apparatus for carrying out the method as claimed in claim 1.

20. A method for post-editing a first image data set obtained using a medical device and a second image data set, the method comprising:
    loading the second image data set so that a post-editing software program of the medical device can extract at least one image attribute from the second image data set;
    buffering the at least one Image attribute; and
    post-editing the first image data set by transferring the at least one buffered image attribute to the first image data set.

21. The method according to claim 20, wherein one of the image data sets and at least one of the buffered image attributes are stored in a file in the medical communication standard DICOM.

22. The method according to claim 20, wherein at least one of the buffered image attributes is allocated to a protocol for image recording using the image producing medical device and wherein a data set obtained with the protocol is displayed using the allocated at least one image attribute.

23. A program recorded on a computer-readable medium, adapted to perform the method of claim 20, when executed on a computer.

* * * * *